United States Patent [19]

Doyle

[11] Plant 5,251

[45] Jun. 26, 1984

[54] PEACH TREE

[76] Inventor: James F. Doyle, 7685 N. Thompson Ave., Clovis, Calif. 93612

[21] Appl. No.: 425,563

[22] Filed: Sep. 28, 1982

[51] Int. Cl.[3] ..... A01H 5/03

[52] U.S. Cl. ..... Plt./42

[58] Field of Search ..... Plt./42

*Primary Examiner*—Robert E. Bagwill

*Attorney, Agent, or Firm*—Huebner & Worrel

[57] ABSTRACT

A peach tree particularly characterized by its fruit, when fully ripe, having very firm, non-melting flesh which, in most fruit, is completely free of color, the free being further characterized by having large showy blossoms and by bearing clingstone fruit which has superior shipping and keeping qualities, which ripens approximately 20 days earlier than fruit of the Nectar Peach Tree (U.S. Plant Pat. No. 86), and which has an attractive skin coloration.

1 Drawing Figure

BACKGROUND OF THE VARIETY

The present invention relates to a new and distinct variety of peach tree broadly characterized by bearing clingstone fruit which has superior shipping and keeping qualities, which is of pleasing flavor and skin coloration, and which has flesh of white or cream coloration, the subject variety being more particularly characterized by its fruit ripening about twenty days earlier than fruit of the Nectar variety (U.S. Plant Pat. No. 86), and by its fruit, when fully ripe, having flesh which is very firm and non-melting and substantially free of coloration. The cultivar name for my new variety is Snowflame.

The Nectar variety of peach tree is well known for its bearing of fruit having a generally white flesh and for its excellent eating qualities and attractive skin coloration. It has been recognized as advantageous to provide a peach tree bearing fruit having the desirable characteristics of fruit of the Nectar variety but having very firm and non-melting flesh which is well suited for canning and having superior shipping and keeping qualities. The flesh of peaches of the Nectar variety is somewhat tinged with pink, especially when fully ripe. However, uniformity in coloration is a characteristic often desired by consumers so that it is advantageous to provide a peach tree bearing fruit with flesh generally free from coloration when fully ripe. In many instances, the time of harvest of peaches greatly influences the price bought on the market, so that it is highly advantageous to provide a variety of peach tree bearing fruit having the desirable eating qualities and general coloration of peaches borne by the Nectar variety, but bearing fruit which ripens substantially earlier when other peaches having those desirable characteristics are not available.

ORIGIN AND ASEXUAL REPRODUCTION OF THE NEW VARIETY

My new variety of peach tree was originated by me as a part of a continuing plant breeding program in an orchard owned by me and located at 7685 N. Thompson Avenue, near the City of Clovis, in the County of Fresno, and in the State of California. I originated the subject variety by germinating an open pollinated seed from the Nectar variety of peach tree (U.S. Plant Pat. No. 86). When the resulting seedling matured, open pollinated seeds therefrom were, in turn, planted in 1974 and the resulting seedlings grafted by me in 1975 at such orchard onto mature peach trees. The fruit and tree characteristics resulting from grafting such seedlings were carefully observed and the subject variety was selected in 1976 as one tree resulting from such grafting. The selected variety was then propagated by me by further grafting in said orchard, and the tree and fruit characteristics from such grafting proved identical to that of the selected tree.

SUMMARY OF THE NEW VARIETY

The subject variety of peach tree bears clingstone fruit having a white or cream colored flesh and attractive exterior coloration. The subject variety has large, showy blossoms and is particularly characterized by its fruits having flesh which is firm and non-melting and which, in most fruit, is completely free of color. The subject variety is distinguished from the Nectar variety of peach tree (U.S. Plant Pat. No. 86), from which the subject variety is derived, in that the Nectar variety has relatively small, non-showy flowers and relatively softer and melting flesh which is tinged with pink or red. As a result of such very firm flesh, fruit of the subject varity is superior in shipping and keeping qualities to fruit of the Nectar variety and is well suited to canning. The fruit of the subject variety ripens approximately twenty days earlier than fruit of the Nectar variety, but the two varieties of peach tree are similar in being vigorous, in having reinform leaf glands, and in bearing fruit of excellent aroma and eating quality.

BRIEF DESCRIPTION OF THE DRAWING

The accompanying drawing is a color photograph of mature peaches of the subject variety together with a typical twig bearing characteristic leaves, one of the peaches being divided substantially at the suture plane to show the flesh and stone characteristics.

DETAILED DESCRIPTION

Referring more specifically to the pomological details of the new and distinct variety of peach tree, the following has been observed under the ecolgoical conditions prevailing in the above-specified orchard near Clovis, Fresco County, Calif. All of the color plate designations are by reference to the Maerz and Paul *Dictionary of Color,* Second Edition, 1950, common descriptive color names also being used.

TREE

Size: Large, with shape and density determined by pruning.

Vigor: Vigorous.

Productivity: Good.

Regularity of bearing: Regular.

Trunk: Medium in size and texture.

Branches: Average in size and texture. New shoots greenish (20-K-7) when young tinged violet (55-H-7) with exposure to sun. Older shoots grey-brown (8-C-8).

Leaves: Large, average dimensions taken from leaves at midpoint of actively growing shoots.

*Average length.*—205 mm.

*Average width.*—52 mm.

*Blade.*—Medium thickness.

*Shape.*—Strongly lanceolate.

*Tip.*—Acuminate, often strongly recurved. Some leaves folded or boated.

*Color.*—Upper leaf surface dark green (24-J9), lower leaf surface lighter green (22-F-7).

*Margin.*—Coarsely crenate with small gland at each depression.

*Petiole.*—Moderate length, 13–15 mm, 2 mm thick.

*Glands.*—Large size and reinform in shape, averaging three in number. Position usually two alternate on petiole and one on base of leaf blade. Light green in color with yellowish center when young, often dried up on older leaves.

*Stipules.*—Present on young leaves, light green in color (17-K-7), 7–8 mm long. Early deciduous.

Flower buds: Medium in size, conic in shape with moderate pubescence.

Flowers: Bloom description made at Clovis, Calif. Mar. 9, 1982.

*First bloom.*—Mar. 6, 1982.

*Full bloom.*—Mar. 11, 1982. Medium to slightly late date of bloom in comparison with other peach varieties.

*Size.*—Medium for species, showy phenotype, 42–47 mm across when fully open.

*Pedicel.*—Short, about 1 mm long. Greenish color (18-K-7) tinged red with exposure. Glabrous, lightly grooved.

*Number of flowers.*—Average 1–2 per node.

*Petals.*—Pink (1-D-2) becoming darker basally with age. Large, broadly ovate to nearly round, 20–22 mm long, 18–20 mm wide, very slightly cupped when fully open. Margin slightly wavy.

*Nectaries.*—Greenish-orange (12-J-9) when young becoming greenish-yellow (12-J-3) with age.

*Stamens.*—Variable length 8–18 mm long. Filaments slender, light pink at anthesis becoming darker with age. Number variable 42 to 57. Anthers medium size, red dorsally, buff ventrally. Pollen abundant — yellow.

*Pistil.*—Length 16 mm, about equal to average stamen in length when flower fully open.

FRUIT

Maturity: Described at eating ripe maturity. Reached in the San Joaquin Valley of California June. 22 to June 27.

Size: Medium to large. Uniform. Cheek diameter average 68 mm. Suture diameter average 68 mm. Axial length average 66 mm.

Form: Symmetrical, uniform, nearly globose in axial aspect. Globose to slightly oblate in lateral aspect.

*Suture.*—A shallow line at times discontinuous near midpoint on ventral suture, extending from base to apex and at times 10–15 mm beyond apex. Discontinuous at apex, with usually a marked depression beyond the pistil point.

*Ventral surface.*—Rounded, occasionally slightly lipped on right or left side. Lips at times unequal but only slightly so.

*Stem cavity.*—Axial aspect oval, elongated in suture plane with suture often visible on both ventral and dorsal sides up to top of dorsal shoulder. Cavity conic. Average width 13 mm, average length 19 mm, average depth 11 mm.

*Base.*—Rounded, very slightly oblique to ventral edge.

*Stem.*—Medium length, average 11 mm.

*Apex.*—Rounded, depressed.

*Pistil point.*—Oblique.

Skin: Medium thickness, medium texture, tenacious to flesh. No observed tendency to crack.

*Color.*—Grounded color cream (17-D-1). 50 to 100% of the fruit surface overlaid with blush red (3-J-10) to dark red (6-K-9), depending on exposure to sunlight.

*Pubescence.*—Short, light in quantity.

Flesh:

*Color.*—White to cream (10-B-1). Most fruit completely free of color in flesh. Surface of pit cavity white to cream.

*Amygdalin.*—Slight.

*Juice.*—Abundant.

*Texture.*—Firm, fine, non-melting.

*Fibers.*—Few, tender.

*Ripening.*—Even.

*Flavor.*—Mild, delicate.

*Aroma.*—Profuse, distinct, very pleasing.

*Eating quality.*—Very good.

Stone: Full clingstone adhering to flesh over entire surface.

*Fibers.*—Moderate length.

*Size.*—Medium, average length 35 mm, average width 26 mm, average breadth 21 mm.

*Form.*—Roughly obovate.

*Base.*—Oblique to ventral suture.

*Apex.*—Rounded with short acute tip.

*Sides.*—Nearly equal. Surface heavily grooved near base. Deep grooves near apex in lateral aspect. Ridges jagged near apex, somewhat eroded near apex along dorsal edge.

*Dorsal edge.*—Fairly narrow with deep groove from base to apex. Upper dorsal edge heavily eroded down one third distance of entire edge from apex.

*Ventral edge.*—Generally full with prominent thin wing at basal end of ventral suture extending out 4–5 mm from body of the stone. Shorter wings evident along remainder of suture, converging apically.

*Color.*—Buff (11-H-6) to brown (14-H-9).

*Splitting tendency.*—Slight tendency to split in some years.

Use: Fresh market and shipping, both local and long distance. Also of considerable merit for use in canning.

Keeping quality: Good. Superior to Nectar.

Shipping quality: Good, of decided superiority to Nectar in this respect.

Resistance to disease and insects: Average. No particular susceptibilities noted.

Although the new variety of peach tree possesses the described characteristics as a result of the growing conditions of Fresno County, California in the San Joaquin Valley, it is to be understood that variations of the usual magnitude in characteristics incident to growing conditions, fertilization, pruning and pest control are to be expected.

Having thus described and illustrated my new variety of peach tree, I claim:

1. A new and distinct variety of peach tree characteritized by bearing clingstone fruit which ripens approximately twenty days earlier than fruit of the Nectar Peach Tree (U.S. Plant Pat. No. 86), having superior shipping and keeping qualities; flesh of a white or cream color (10-B-1); skin of cream ground color (17-O-1) overlaid with blush red (3-J-10) to dark red (6-K-9); and large, showy blossoms; and such tree being particularly characterized as to novelty by bearing peaches which, when fully ripe, have flesh which is very firm and nonmelting and virtually completely free of color.

* * * * *

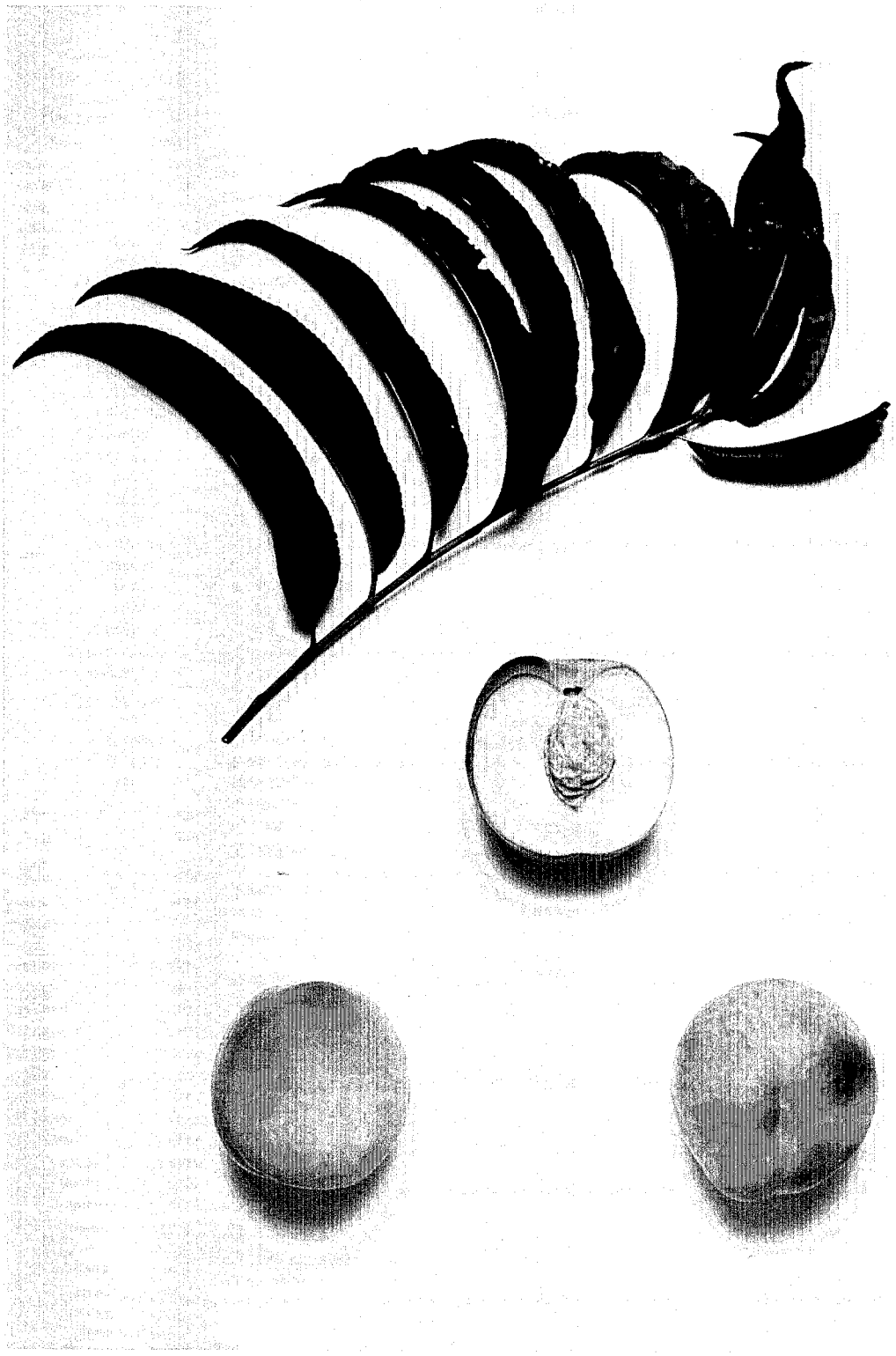

UNITED STATES PATENT AND TRADEMARK OFFICE

CERTIFICATE OF CORRECTION

PATENT NO. : PP. 05,251

DATED : June 26, 1984

INVENTOR(S) : James F. Doyle

It is certified that error appears in the above-identified patent and that said Letters Patent are hereby corrected as shown below:

In the Abstract, line 3, delete "free" 2nd occurrence and substitute --tree--.

Column 2, line 44, delete "Fresco" and substitute ---Fresno---.

Column 3, line 21, delete "Q4-J9)" and substitute ---(24-J-9)---.

Column 4, line 24, delete "Grounded" and substitute ---Ground---.

Signed and Sealed this

*Sixteenth* Day of *October 1984*

[SEAL]

*Attest:*

GERALD J. MOSSINGHOFF

*Attesting Officer*

*Commissioner of Patents and Trademarks*